US011524025B2

(12) United States Patent
Tzoumaki et al.

(10) Patent No.: US 11,524,025 B2
(45) Date of Patent: Dec. 13, 2022

(54) COMPOSITION FOR USE IN THE PREVENTION OR TREATMENT OF SALMONELLOSIS

(71) Applicant: NutriLeads B.V., Wageningen (NL)

(72) Inventors: Maria Tzoumaki, Wageningen (NL); Ruud Albers, Rockanje (NL)

(73) Assignee: NutriLeads B.V., Wageningen (NL)

(*) Notice: Subject to any disclaimer, the term of this patent is extended or adjusted under 35 U.S.C. 154(b) by 149 days.

(21) Appl. No.: 16/889,474

(22) Filed: Jun. 1, 2020

(65) Prior Publication Data
US 2020/0289545 A1 Sep. 17, 2020

Related U.S. Application Data

(63) Continuation of application No. PCT/NL2017/050807, filed on Dec. 4, 2017.

(51) Int. Cl.
A61K 31/715 (2006.01)
A61P 31/04 (2006.01)
A61K 31/07 (2006.01)
A23K 20/163 (2016.01)
A23K 50/00 (2016.01)
A23K 20/147 (2016.01)
A23K 20/158 (2016.01)
A23K 20/174 (2016.01)
A23K 20/20 (2016.01)
A23K 50/30 (2016.01)
A23K 50/75 (2016.01)
A23L 33/125 (2016.01)
A23L 33/00 (2016.01)
A23L 33/155 (2016.01)

(52) U.S. Cl.
CPC .......... A61K 31/715 (2013.01); A23K 20/147 (2016.05); A23K 20/158 (2016.05); A23K 20/163 (2016.05); A23K 20/174 (2016.05); A23K 20/20 (2016.05); A23K 50/30 (2016.05); A23K 50/75 (2016.05); A23L 33/125 (2016.08); A23L 33/155 (2016.08); A23L 33/40 (2016.08); A61P 31/04 (2018.01); A23V 2002/00 (2013.01)

(58) Field of Classification Search
CPC ...... A61K 31/715; A23K 50/75; A23K 50/30; A23K 20/147; A23L 33/125; A23L 33/155; A23V 2200/324
USPC ........................................................ 514/54
See application file for complete search history.

(56) References Cited

U.S. PATENT DOCUMENTS

| 2002/0022601 A1 | 2/2002 | Konno et al. |
| 2004/0072791 A1 | 4/2004 | Kunz et al. |
| 2010/0047209 A1 | 2/2010 | Stanton et al. |
| 2011/0112048 A1 | 5/2011 | Cox et al. |
| 2013/0137757 A1 | 5/2013 | Koide |
| 2014/0275233 A1 | 9/2014 | Heiman |
| 2014/0288021 A1 | 9/2014 | Freitas et al. |
| 2016/0151485 A1 | 6/2016 | Albers et al. |
| 2016/0250625 A1 | 9/2016 | Kanaya et al. |

FOREIGN PATENT DOCUMENTS

| CN | 102784193 A | 11/2012 |
| KR | 2017/053144 A | 5/2017 |
| WO | WO-01/76609 A1 | 10/2001 |
| WO | WO-2004/084652 A1 | 10/2004 |
| WO | WO-2005/095463 A1 | 10/2005 |
| WO | WO 2011/069781 A1 | 6/2011 |
| WO | WO-2011/136634 A1 | 11/2011 |
| WO | WO-2012/148277 A1 | 11/2012 |
| WO | WO-2015/192247 A1 | 12/2015 |
| WO | WO-2016/132130 A1 | 8/2016 |

OTHER PUBLICATIONS

Wright et al, Emerging Infectious Diseases, 2005, 11(8), 1235-1241.*
Alaa Abdul Aziz: "The effect of the Capsicum annuum in the diet of broilers on the isolation and shedding rate of Salmonella paratyphoid." Al-Qadssiya University,Vet. Med. Coll. Kufa Journal For Veterinary Medical sciences, vol. 1, No. 1, 2010.
Anne Petersen et al: "Some putative prebiotics increase the severity or Salmonella entenca serovar Typhimurium infection in mice", BMC Microbiology 2009, 9:245, Nov. 30, 2009.
Broxterman Suzanne E et al: "Acetylated pectins in raw and heat processed carrots", Carbohydrate Polymers, vol. 177, Aug. 30, 2017 (Aug. 30, 2017), pp. 58-66, XP085205714, ISSN: 0144-8617, DOI: 10.1016/J.CARBPOL.2017.08.118.
Bryony N. Parsons et al: "Dietary Supplementation with Soluble Plantain Non-Starch Polysaccharides Inhibits Intestinal Invasion of Salmonella Typhimurium in the Chicken". PLOS One, vol. 9, No. 2,Feb. 3, 2014 (Feb. 3, 2014), p. e87658, XP055496849,DOI: 10.1371/journal.pone.0087658.
International Search Report dated Aug. 13, 2018 received in International Application No. PCT/NL2018/050807, 4 pages.

(Continued)

Primary Examiner — Ganapathy Krishnan
(74) Attorney, Agent, or Firm — Gilberto Villacorta; Foley & Lardner LLP

(57) ABSTRACT

The invention relates to a composition for use in the prevention or treatment of Salmonellosis in animals, said use comprising administering the composition to the animal, wherein the composition contains at least 0.01% by weight of dry matter of rhamnogalacturonan I (RG-I) polysaccharides having a molecular weight of more than 2 kDa and having a backbone consisting of galacturonic acid residues and rhamnose residues, said rhamnose residues being contained in alpha(1→4)-galacturonic-alpha(1→2)-rhamnose residues, wherein the molar ratio of galacturonic acid residues to rhamnose residues in the RG-I polysaccharides is within the range of 50:1 to 1:1.
The use of RG-I polysaccharides in the treatment or prevention of Salmonellosis provides an alternative for the widespread use of antibiotics. Furthermore, these RG-I polysaccharides may be used to prevent or treat Salmonellosis caused by Salmonella strains with resistance to antibiotics.

13 Claims, 2 Drawing Sheets

(56) References Cited

OTHER PUBLICATIONS

International Search Report dated Jan. 4, 2019 received in corresponding International Application No. PCT/EP2018/079055, 5 pages.
International Search Report dated Jan. 4, 2019 received in corresponding International Application No. PCT/EP2018/079058, 5 pages.
Kirtschev [Kirchev] N A et al: Pectins of some carrot (*Daucus carota*) varieties. (translated) TIOL—Ueber Pektinstoffe einiger Vertreter der Art "*Daucus Carota*". Zeitschrift Fuer Lebensmittel-Untersuchung und—Forschung, vol. 170, No. 1, 1980, pp. 31-33, XP002776946.
Merve Kaya et al: "Characterization of citrus pectin samples extracted under different conditions: influence of acid type and pH of extraction", Annals of Botany., vol. 114, No. 6, Jul. 31, 2014 (Jul. 31, 2014), pp. 1319-1326, XP055535664, GB, ISSN: 0305-7364, DOI: 10.1093/aob/mcu150.
Morris GA et al: "Physical characterisation of the rhamnogalacturonan and homogalacturonan fractions of sugar beet (*Beta vulgaris*) pectin", Carbohydrate Polymers, Applied Science Publishers, Ltd. Barking, GB, vol. 82, No. 4, Nov. 11, 2010 (Nov. 11, 2010), pp. 1161-1167, XP027266305, ISSN: 0144-8617 [retrieved on Sep. 7, 2010] paragraphs [02.2], [03.5]; example fig. 1.
Nastaran Khodaei et al: "Extraction and structural characterisation of rhamnogalacturonan I-type pectic polysaccharides from potato cell wall", Food Chemistry, vol. 139, No. 1-4, Feb. 10, 2013 (Feb. 10, 2013), pp. 617-623, XP55244701, NL, ISSN: 0308-8146, DOI: 10.1016/j.foodchem.2013.01.110 cited in the application paragraphs [02.1], [2.2.1], [2.2.2], [03.1], [03.2], [03.3], [03.4], [0004].
Park Hye-Ryung et al: "Structural 1-12, elucidation of antimetastatic 14-20 rhamnogalacturonan II from the pectinase digest of citrus peels (*Citrus unshiu*)", International Journal of Biological Macromolecules, Els ev i er BV, NL, vol. 94, Sep. 29, 2016 (Sep. 29, 2016), pp. 161-169, XP029818798, ISSN: 0141-8130, DOI: 10.1016/J.IJBIOMAC.2016.09.100 paragraphs [0001], [02 .1], [02. 2], [03. 1] ; figure 1.
Ridley B L et al: "Pectins: structure, biosynthesis, and oligogalacturonide-related signaling", Phytochemi, Pergamon Press, GB, vol. 57, No. 6, Jul. 1, 2001 (Jul. 1, 2001), pp. 929-967, XP004245805, ISSN: 0031-9422, DOI: 10.1016/S0031-9422(01)00113-3.

Babbar et al., "Pectic oligosaccharides from agricultural by-products: production, characterization and health benefits", Critical Reviews in Biotechnology, vol. 36, No. 4, 2015, pp. 594-606.
Chatterjee et al., "Effect of Fruit Pectin on Growth of Lactic Acid Bacteria", Journal of Probiotics & Health, vol. 4, No. 2, 2016 (6 pages).
De Weirdt et al., "Human faecal microbiota display variable patterns of glycerol metabolism", FEMS Microbiology Ecology, vol. 74, 2010, pp. 601-611 (11 pages).
Edgar, "Search and clustering orders of magnitude faster than BLAST", Bioinformatics, vol. 26, No. 19, 2010, pp. 2460-2461 (2 pages).
Gomez et al. "Prebiotic potential of pectins and pectic oligosaccharides derived from lemon peel wastes and sugar beet pulp: A comparative evaluation", Journal of Functional Foods, vol. 20, 2016, pp. 108-121 (14 pages).
Gregory et al. "QIIME allows analysis of high-throughput community sequencing data" Nature Methods, vol. 7, No. 5, 2010, pp. 335-336 (4 pages).
International Search Report issued for PCT Appl. Ser. No. PCT/EP2018/074127 dated Dec. 11, 2018 (4 pages).
Khodaei et al., "Enzymatic extraction of galactan-rich rhamnogalacturonan I from potato cell wall by-product", LWT—Food Science and Technology, vol. 57, 2014, pp. 207-216 (10 pages).
Kim et al., "Effect of arabinoxylan- and rhamnogalacturonan I-rich polysaccharides isolated from young barley leaf on intestinal immunostimulatory activity", Journal of Functional Foods, vol. 35, 2017, pp. 384-390 (7 pages).
Reeves, et al. "AIN-93 Purified Diets for Laboratory Rodents: Final Report of the American Institute of Nutrition Ad Hoc Writing Committee on the Reformulation of the AIN-76A Rodent Diet" Journal of Nutrition, vol. 123, No. 11, 1993, pp. 1939-1951 (15 pages).
"Common Cold", Mayo Clinic; available at https://www.mayoclinic.org/diseases-conditionals/common-cold/symptoms-causes/syc-20351605; last accessed Jun. 2022.
"Prevent" definition, WordNet Search 3.1; available at wordnetweb.princeton.edu/perl/webwn; last accessed Jan. 2021 (1 page).
Bonnin et al., "Pectin-modifying enzymes and pectin-derived materials: applications and impacts", Appl Microbiol Biotechnol (2014) 98: 519-532 (14 pages).

\* cited by examiner

COMPOSITION FOR USE IN THE PREVENTION OR TREATMENT OF SALMONELLOSIS

CROSS-REFERENCE TO RELATED APPLICATIONS

This application is a continuation of International Application No. PCT/EP2017/050807, filed Dec. 4, 2017, which is hereby incorporated by reference in its entirety.

TECHNICAL FIELD OF THE INVENTION

The present invention relates to the prevention of Salmonellosis in animals. More particularly, the invention relates to the prevention or treatment of Salmonellosis in animals by administering such animals a composition that contains rhamnogalacturonan I (RG-I) polysaccharides having a molecular weight of more than 2 kDa and having a backbone consisting of galacturonic acid residues and rhamnose residues, said rhamnose residues being contained in alpha (1→4)-galacturonic-alpha(1→2)-rhamnose residues, wherein the molar ratio of galacturonic acid residues to rhamnose residues in the RG-I polysaccharides is within the range of 50:1 to 1:1.

The aforementioned RG-I polysaccharides may be isolated from fruit and vegetables, such as apple, bell pepper, bilberry, carrot, citrus fruit, grape, sugar beet, olives, pea or potato.

BACKGROUND OF THE INVENTION

Salmonellosis is an infectious disease of humans and animals caused by organisms of the two species of *Salmonella* (*Salmonella enterica*, and *S. bongori*). Although primarily intestinal bacteria, salmonellae are widespread in the environment and commonly found in farm effluents, human sewage and in any material subject to faecal contamination. *Salmonella* organisms are aetiological agents of diarrhoeal and systemic infections in humans, most commonly as secondary contaminants of food originating from animals and the environment, usually as a consequence of subclinical infection in food animals leading to contamination of meat, eggs, and milk or secondary contamination of fruits and vegetables that have been fertilised or irrigated by faecal wastes.

Human salmonellosis is one of the most common and economically important zoonotic diseases. *Salmonella* organisms may also be found in animal feedstuffs, causing subclinical gastro-intestinal carriage or infectious disease in animals, particularly poultry and pigs. Salmonellosis has been recognised in all countries, but appears to be most prevalent in areas of intensive animal husbandry, especially in pigs and calves and some types of poultry reared in confinement. Several serovars are host specific (e.g. *S. abortusovis* in sheep or *S. typhi* in humans) or host adapted (e.g. *S. choleraesuis* in pigs and *S. dublin* in cattle).

The disease can affect all species of domestic animals; young animals and pregnant and lactating animals are the most susceptible. Enteric disease is the commonest clinical manifestation, but a wide range of clinical signs, which include acute septicaemia, abortion, arthritis and respiratory disease, may be seen. *Salmonella* infection can adversely affect digestion and can impair growth of young animals. Many animals, especially pigs and poultry, may also be infected but show no clinical illness. Such animals may be important in relation to the spread of infection between flocks and herds and as sources of food contamination and human infection.

The WHO provides information on the development of appropriate measures for the prevention and control of food-borne diseases, including *Salmonella* infections, of humans. The most common vehicles of infection are eggs and egg products, poultry meat and meat from other food animals, and meat products. *Salmonella enteritidis* and *Salmonella. typhimurium* are the most widespread serovars in many European countries. *Salmonella typhimurium* is the dominant serovar in North America.

A monophasic variant of *S. typhimurium* (S.4,5,12:i:-DT193 with resistance to ampicillin, streptomycin, sulphonamides and tetracycline) has emerged in pigs and caused outbreaks of salmonellosis in humans in several countries worldwide, and there are several other emergent monophasic S.4,5,12:i:- and S.4,12:i:- strains with varying resistance patterns that have been recognised in various animal species and humans in many countries in recent years.

Antimicrobial resistance within a wide range of infectious agents is a growing public health threat of broad concern to countries and multiple sectors. Increasingly, governments around the world are beginning to pay attention to a problem so serious that it threatens the achievements of modern medicine. A post-antibiotic era—in which common infections and minor injuries can kill—far from being an apocalyptic fantasy, is instead a very real possibility for the 21st century.

The use of antibiotics in animal husbandry—including in livestock, poultry and fish farming—are leading to increasing recognition that urgent action is needed to avoid inappropriate use, and to reduce antibiotic usage in animal husbandry and aquaculture, as well as in humans.

Petersen et al. (*Some putative prebiotics increase the severity of Salmonella enterica serovar typhimurium infection in mice*, BMC Microbiology (2009), 9:245) describe the outcome of a study in which it was examined whether *S. typhimurium* SL1344 infection in mice could be prevented by administration of dietary carbohydrates with different structures and digestibility profiles. BALB/c mice were fed a diet containing 10% of either of the following carbohydrates: inulin, fructo-oligosaccharide, xylo-oligosaccharide, galacto-oligosaccharide, apple pectin, polydextrose or beta-glucan for three weeks prior to oral *Salmonella* challenge ($10^7$ CFU) and compared to mice fed a cornstarch-based control diet. The mice fed with diets containing fructo-oligosaccharide or xylo-oligosaccharide had significantly higher ($P<0.01$ and $P<0.05$) numbers of *S. typhimurium* SL1344 in liver, spleen and mesenteric lymph nodes when compared to the mice fed with the cornstarch-based control diet. Significantly increased amounts ($P<0.01$) of *Salmonella* were detected in ileal and fecal contents of mice fed with diets supplemented with apple pectin, however these mice did not show significantly higher numbers of *S. typhimyrium* in liver, spleen and lymph nodes than animals from the control group ($P<0.20$).

Parsons et al. (*Dietary Supplementation with Soluble Plantain Non-Starch Polysaccharides Inhibits Intestinal Invasion of Salmonella typhimurium in the Chicken*, PLOS ONE, February 2014, Volume 9, Issue 2, e87658) report that dietary plantain fibre prevents invasion of the chicken intestinal mucosa by *Salmonella*. In vivo experiments were performed with chicks fed from hatch on a pellet diet containing soluble plantain NSP (0 to 200 mg/d) and orally infected with *S. typhimurium* 4/74 at 8 d of age. In vivo dietary supplementation with plantain NSP 50 mg/d reduced invasion by *S. typhimurium*, as reflected by viable bacterial counts from splenic tissue, by 98.9% (95% Cl, 98.1-99.7; P<0.0001). In vitro studies confirmed that plantain NSP (5-10 mg/ml) inhibited adhesion of *S. typhimurium* 4/74 to a porcine epithelial cell-line (73% mean inhibition (95% Cl, 64-81); P,0.001) and to primary chick caecal crypts (82% mean inhibition (95% Cl, 75-90); P,0.001). The inhibitory activity of plantain NSP lay mainly within the acidic/pectic (homogalacturonan-rich) component.

Aziz (*The effect of the Capsicum annuum in the diet of broilers on the isolation and shedding rate of Salmonella paratyphoid*, Kufa Journal For Veterinary Medical Sciences Vol.(1) No. (1) 2010, 28-38) describes a study in which the inhibitory effect of *C. annuum*, as a possible alternative to antibiotics against the challenge dose of *S. typhimurium* in broiler chickens was investigated. The results showed that the use of mixed diet with *C. annuum* at percent 1% and 2%, were effective against *S. typhimurium* infection.

WO 2011/136634 describes the use of a pectin degradation product for the prevention and/or treatment of weight reduction in subjects suffering from *salmonella* infection or susceptible to *salmonella* infection.

US 2010/0047209 describes a probiotic composition to alleviate *Salmonella* infection in farm animals, said probiotic composition comprising one or more microbial cultures selected from the group consisting of *Lactobacillus murinus, L. pentosus, L. salivarius* sub-species *salivarius*, and *Pediococcus pentosaceus*.

Pectin is a structural hetero polysaccharide that is present in the primary cell walls of terrestrial plants.

Pectic polysaccharides are a heterogeneous group of polysaccharides comprising varying amounts of the following polysaccharide components:
(i) homogalacturonan (HG),
(ii) xylogalacturonan (XG),
(iii) apiogalacturonan (AG)
(iv) rhamnogalacturonan-I (RG-I), and
(v) rhamnogalacturonan-II (RG-II).

FIG. 1 provides a schematic representation of the structure of pectic polysaccharides, including the aforementioned 5 polysaccharide components. It is noted that the polysaccharide components AG, XG and RG-II typically represent only a minor fraction of pectic polysaccharides.

The polysaccharide components HG, AG, XG and RG-II each comprise a backbone that consists of a linear chain of α-(1-4)-linked D-galacturonic acid monosaccharide units.

Only RG-I comprises a backbone that consists of a linear chain of the repeating disaccharide units: 4)-α-D-galacturonic acid-(1,2)-α-L-rhamnose-(1. A schematic representation of the structure of RG-I is shown in FIG. 2.

Pectic polysaccharide composition and fine structure vary widely depending on the plant source and the extraction conditions applied. The homogalacturonan domain can have a length of up to about 100 consecutive D-GalA residues. The RG-I domain containing the side chains is usually called the 'ramified region' or 'hairy region', while the homogalacturonan domain (connected to RG-I domains) is not typically substituted with glycosides/or glycosidic side chains.

The GalA residues in RG-I are linked to the Rha residues via the 1 and 4 positions, while the Rha residue is linked to the GalA residue via the anomeric and O-2 positions. In general about 20-80% of the Rha residues is branched at the O-4 position (depending on the plant source and the method of isolation), with neutral and acidic side chains. These side chains consist mainly of Ara and Gal residues linked in various manners, constituting polymers known as arabinans, arabinogalactan I (AG-I) and/or AG-II. AG I is composed of a beta-(1,4)-linked D-Gal backbone with substitutions at O-3 of alpha-L-arabinosyl groups; the GaI backbone can have interspacing alpha(1,5)-L-Ara units. AG-II consists of highly ramified galactan with predominantly interior beta(1, 3)-linked D-Gal with substitutions of short (1,6)-linked chains exteriorly. The latter has further attachments of (1,3)- and/or alpha(1,5)-linked L-Ara. The side chains may be linear or branched, and some of these side chains may be terminated with alpha-L-fucosides, beta-D-glucuronides, and 4-O-methyl beta-D-glucuronyl residues.

WO 2011/069781 describes a polysaccharide that is capable of modulating immune response, said polysaccharide being obtained from plants of the species *Camellia sinensis*, wherein the backbone of the polysaccharide comprises alternating rhamnogalacturonan-I domains and alpha (1,4)-linked polygalacturonic acid or alpha(1,4)-linked oligogalacturonic acid domains, wherein the molar ratio of galacturonyl acid residues to rhamnosyl residues in the backbone of the polysaccharide ranges from 2.5:1 to 1:1, and wherein the polysaccharide has a molecular weight of at least 70 kDa.

SUMMARY OF THE INVENTION

The inventor has discovered that Salmonellosis in animals may be prevented or treated very effectively by administering this animals a composition that contains a rhamnogalacturonan I (RG-I) polysaccharide having a molecular weight of more than 2 kDa and having a backbone consisting of galacturonic acid residues and rhamnose residues, said rhamnose residues being contained in alpha(1→4)-galacturonic-alpha(1→2)-rhamnose residues, wherein the molar ratio of galacturonic acid residues to rhamnose residues in the RG-I polysaccharides is within the range of 50:1 to 1:1.

Accordingly one aspect of the present invention relates to the use of a composition containing at least 0.01% by weight of dry matter of the RG-I polysaccharides in the prevention or treatment of Salmonellosis in animals, said use comprising administering the composition to the animal.

The use of RG-I polysaccharides in the prevention or treatment of Salmonellosis provides an alternative for the widespread use of antibiotics. Furthermore, these RG-I polysaccharides may be used to prevent or treat Salmonellosis caused by *Salmonella* strains with resistance to antibiotics.

The RG-I polysaccharides that are employed in accordance with the present invention may suitably be isolated from fruit and vegetables, such as apple, bell pepper, bilberry, carrot, citrus fruit, grape, sugar beet, olive, pea and potato. WO 2012/148277 describes an isolation method that can be used to isolate the RG-I polysaccharide.

Another aspect of the present invention relates to a method of preparing an edible composition, said method comprising mixing one or more edible ingredients with a polysaccharide component containing at least 5% by weight of dry matter of the RG-I polysaccharide.

DETAILED DESCRIPTION OF THE INVENTION

Figure 1:
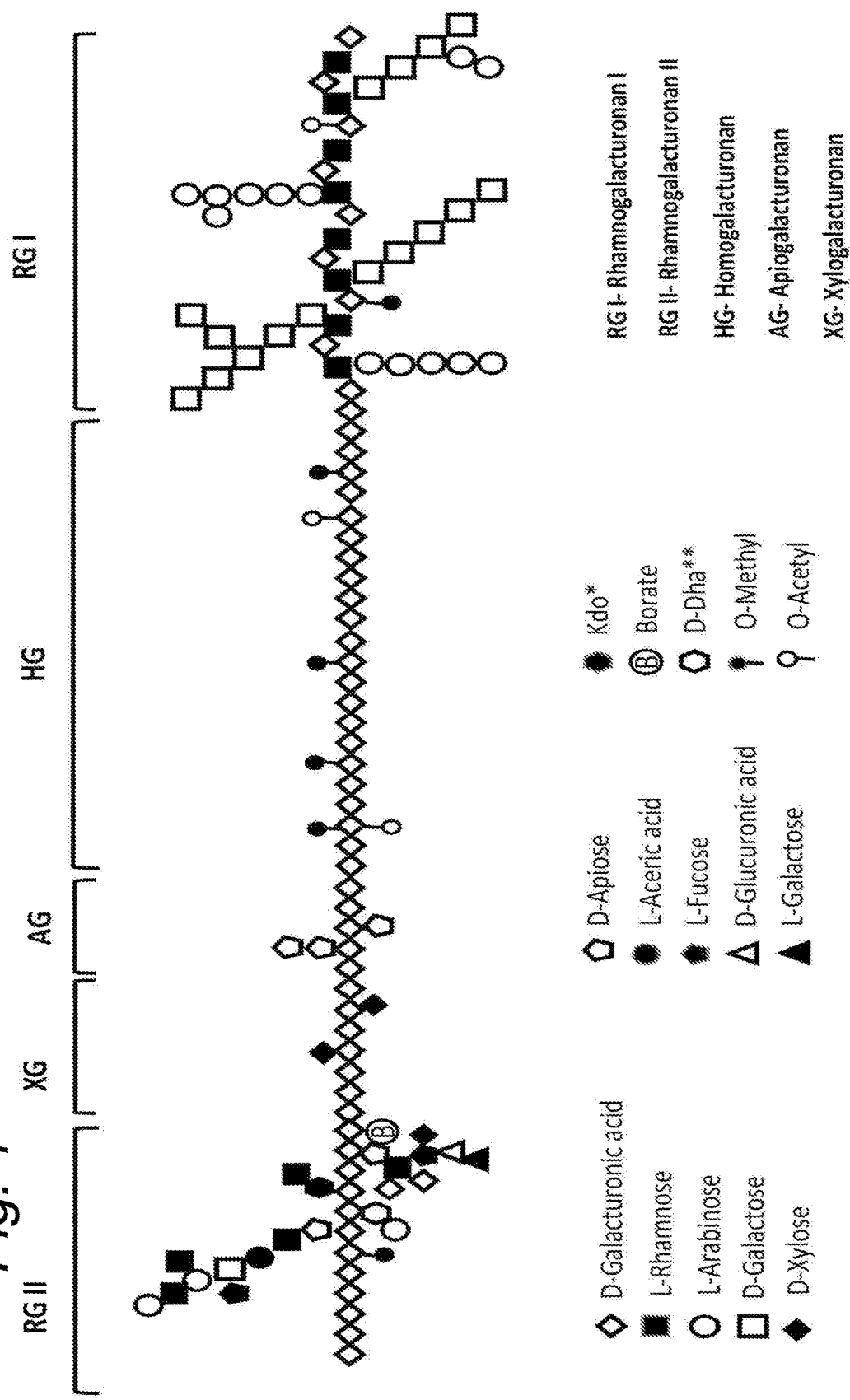
FIG. 1 provides a schematic representation of the structure of pectic polysaccharides, including its 5 polysaccharide components.
Figure 2:
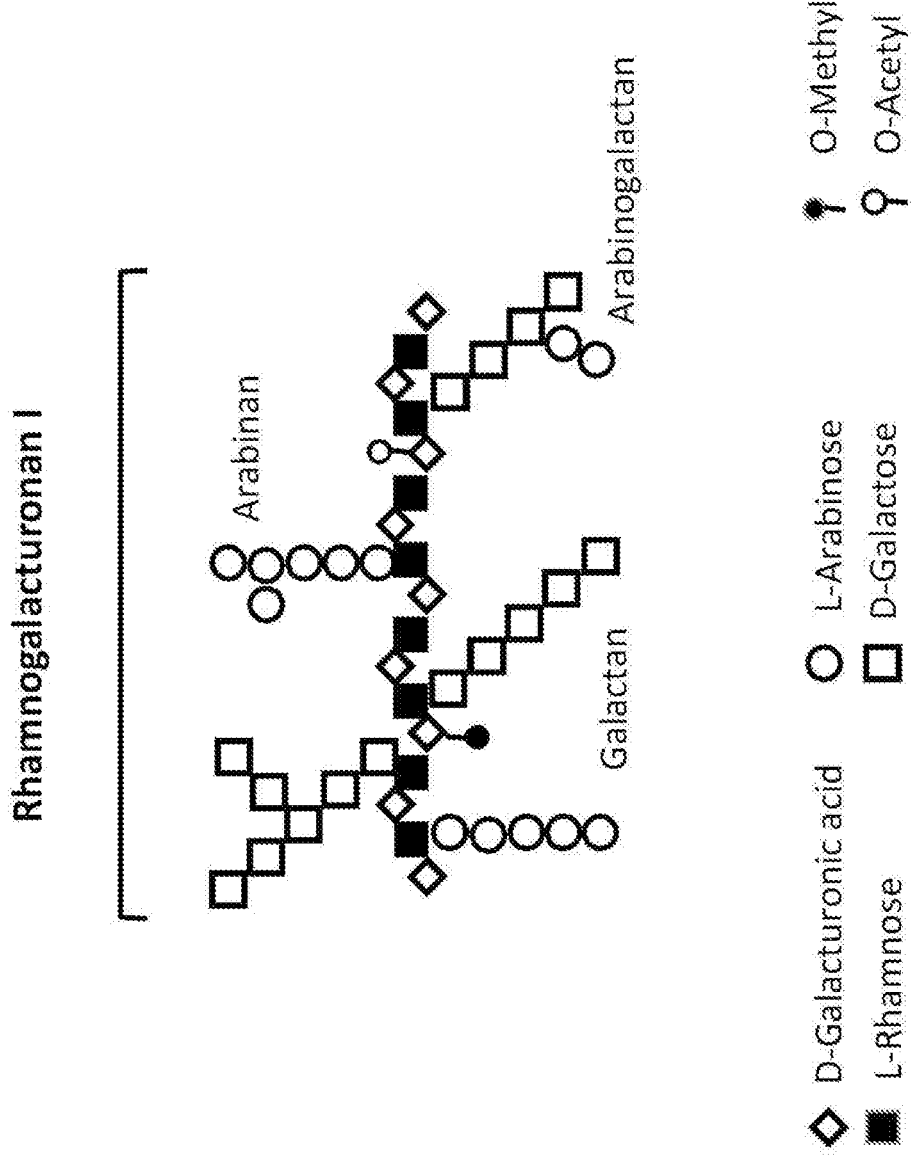
FIG. 2 provides a schematic representation of the structure of RG-I, which comprises a backbone that consists of a linear chain of the repeating disaccharide units: 4)-α-D-galacturonic acid-(1,2)-α-L-rhamnose-(1.

A first aspect of the present invention relates to a composition for use in the prevention or treatment of Salmonellosis in animals, said use comprising administering the composition to the animal, wherein the composition contains at least 0.01% by weight of dry matter of rhamnogalacturonan I (RG-I) polysaccharides having a molecular weight of more than 2 kDa and having a backbone consisting of galacturonic acid residues and rhamnose residues, said rhamnose residues being contained in alpha(1→4)-galacturonic-alpha(1→2)-rhamnose residues, wherein the molar ratio of galacturonic acid residues to rhamnose residues in the RG-I polysaccharides is within the range of 50:1 to 1:1.

The term "Salmonellosis" as used herein refers to an infection caused by Salmonella bacteria.

The term "Salmonella" as used herein refers to a genus of rod-shaped (bacillus) gram-negative bacteria of the Enterobacteriaceae family. The two species of Salmonella are S. enterica and S. bongori. S. enterica subspecies are found in warm-blooded animals, and in the environment. S. bongori is restricted to cold-blooded animals.

The term "animal" as used herein refers to vertebrates, including humans.

The term "branched polysaccharide" as used herein refers to a polysaccharide comprising a linear backbone chain of monosaccharide units bound together by glycosidic linkages, wherein at least one of the monosaccharide units within the backbone chain carries a sidechain of one or more glycosidically linked monosaccharide units.

As used herein, the terms "backbone chain" and "backbone" are synonyms.

The term "pectic polysaccharide" as used herein refers to optionally branched polysaccharides having a molecular weight of more than of 2 kDa and comprising a backbone that consists of galacturonic acid residues and rhamnose residues, said rhamnose residues being contained in alpha (1→4)-galacturonic-alpha(1→2)-rhamnose residues.

The term "stretch" as used herein refers to a sequence of two glycosidically linked monosaccharide units within the backbone of a polysaccharide, excluding any sidechains that are attached thereto.

The term "domain" as used herein refers to a stretch plus any sidechains that are attached to said stretch.

The term "rhamnogalacturonan-I stretch" or "RG-I stretch" refers to a stretch consisting of galacturonic acid (GalA) and rhamnose (Rha) pairs, wherein the GalA residues are linked to the Rha residues via the 1 and 4 positions, while the Rha residues are linked to the GalA residue via the anomeric and O-2 positions, i.e. alternating alpha(1→4)-galacturonic-alpha(1→2)-rhamnose residues. The RG-I domain can comprise side chains such as, for example galactan, arabinan and arabinogalactan side chains.

The term "rhamnogalacturonan-I polysaccharide" or "RG-I polysaccharide" refers to optionally branched pectic polysaccharides that comprise a backbone that contains one or more rhamnogalacturonan-I stretches.

The term "alpha(I,4)-linked galacturonic acid stretch" refers to a stretch consisting of alpha(1→4)-galacturonic residues.

Besides RG-I domains, the RG-I polysaccharides of the present invention may contain one or more of the following domains:

homogalacturonan (HG),
xylogalacturonan (XG),
apiogalacturonan (AG)
rhamnogalacturonan-II (RG-II).

The domains XG, AG and RG-II typically represent only a minor fraction of the RG-I polysaccharides.

The HG domains, XG domains, AG and RG-II domains that are optionally present in the RG-I polysaccharides of the present invention comprise a backbone that consists of a linear chain of two or more α-(1-4)-linked D-galacturonic acids.

HG domains do not contain any sidechains. The carboxyl groups of galacturonic acid residues within the backbone of HG domains may be esterified. Galacturonic acid may be esterified either by methyl or acetyl groups, forming methyl or acetyl esters, respectively.

The backbone of XG domains contains one or more sidechains in the form of D-xylose.

The backbone of AG domains contains one or more sidechains that are composed of one or more D-apiose residues.

The backbone of RG-II contains one or more side chains that are not exclusively composed of D-xylose or D-apiose. The carboxyl groups of galacturonic acid residues within the backbone of RG-II domains may be esterified. Galacturonic acid may be esterified either by methyl or acetyl groups, forming methyl or acetyl esters, respectively.

The terminology "degree of acetylation" refers to the number of acetyl residues per galacturonic acid residue, expressed as a percentage.

The terminology "degree of methylation" refers to the number of methyl residues per galacturonic acid residue, expressed as a percentage.

The concentration of different polysaccharides and their monosaccharide composition can be determined by analytical techniques known to the skilled person. After acid hydrolysis (methanolysis), the monosaccharide composition of neutral sugars, can suitably be determined by High Performance Anion Exchange Chromatography combined with Pulse Amperometric Detection (HPAEC-PAD).

Uronic acids (Galacturonic acid being the dominant of uronic acids) were determined by using the colorimetric m-hydroxydiphenyl assay.

The molecular size distribution can be determined by High Performance Size-Exclusion Chromatography using refractive index (RI) detection (concentration).

The above mentioned analytical methods are described in: Analytical Biochemistry Vol. 207, Issue 1, 1992, pg 176 (for neutral sugar analysis) and in Mol. Nutr. Food Res., Vol 61, Issue 1, 2017, 1600243 (for the Uronic acid analysis and the molecular size distribution).

All percentages mentioned herein, unless otherwise stated, refer to the percentage by weight.

The present invention encompasses the use of the RG-I polysaccharides composition to prevent or treat Salmonellosis. In a particularly preferred embodiment of the present invention the RG-I polysaccharides containing composition is administered to animals to prevent Salmonellosis.

The benefits of the present invention are particularly appreciated when the RG-1 polysaccharide composition is administered to animals that have not (yet) been infected with Salmonellosis. Thus, clinical illness resulting from Salmonellosis may be prevented or at least the severity of the clinical illness may be reduced.

The prevention or treatment of Salmonellosis in accordance with the present invention can advantageously be employed in farm animals to optimize feed utilization and growth.

The RG-I polysaccharides containing composition preferably contains at least 0.03%, more preferably 0.1-10% and most preferably 0.2-5% by weight of dry matter of the RG-I polysaccharides as defined herein.

The RG-I polysaccharides are believed to be particularly effective in the prevention or treatment of Salmonellosis if it is no longer entangled in the matrix of cell wall material. Accordingly, in a particularly preferred embodiment, the RG-I polysaccharides containing composition of the present invention contains at least 0.01% by weight of dry matter, more preferably at least 0.03% by weight of dry matter, even more preferably at least 0.1% by weight of dry matter and most preferably at least 0.2% by weight of dry matter of readily water-soluble RG-I polysaccharides. The concentration of readily water-soluble RG-I polysaccharides in the RG-I polysaccharides containing composition can be determined by combining 100 ml of demineralized water (20° C.) with a sufficient amount of the RG-I polysaccharides containing composition to provide 2.5 grams of dry matter, followed by stirring for 5 minutes and filtration over a 100 μm filter. The RG-polysaccharide in the filtrate is readily water-soluble RG-I polysaccharide.

In accordance with a particularly preferred embodiment of the present invention the present composition is administered to the animal at least once daily during a period of at least 3 days in an amount providing at least 1 mg RG-I polysaccharides per kg of bodyweight per day. More preferably, an amount of at least 10 mg RG-I polysaccharides per kg of bodyweight per day, even more preferred at least 100 mg/kg of bodyweight per day, most preferred at least 250 mg RG-I polysaccharides per kg of bodyweight per day is provided during a period of at least 7 days, most preferably during a period of at least 14 days, by administering the composition containing the RG-I polysaccharide at least once daily.

In accordance with another preferred embodiment, the RG-I polysaccharides containing composition is administered to the animal during a period of at least 21 days, to provide the RG-I polysaccharides in an amount of at least 1 mg RG-I polysaccharides per kg of bodyweight per day, more preferably 50-500 mg RG-I polysaccharides per kg of bodyweight per day.

The RG-I polysaccharides containing composition that is administered to the animal preferably is a food or feed composition containing protein, fat and minerals. Typically, the compositions contains between 10 and 60 en % protein and between 5 and 50 en % fat and between 15 and 90 en. % carbohydrates and between 0 and 10 wt. % ash for animals such as pigs, calves and poultry.

The RG-I polysaccharides containing composition preferably contains a combination of vitamins. More particularly, said composition contains:
1,000-2,500 IU/kg of vitamin A;
0.1-10 mcg/kg of vitamin B12;
100-350 IU/kg of vitamin D;
2-20 IU/kg of vitamin E; and
0.25-0.60 mg/kg of vitamin K.

According to another preferred embodiment, the RG-I polysaccharides containing composition is administered to an animal that does not already suffer from Salmonellosis. As shown in the examples, the RG-I polysaccharides containing composition, when administered prior to infection with *Salmonella*, is particularly effective in increasing the animal's capability of quickly recovering from Salmonellosis.

The RG-I polysaccharides containing composition of the present invention can effectively be used to prevent or treat Salmonellosis caused by *S. enterica*. Even more preferably, the composition is used to prevent or treat Salmonellosis caused by *S. enteritidis* or *S. typhimurium*. Accordingly, one advantageous embodiment of the present invention relates to the prevention or treatment of Salmonellosis caused by *S. enteritidis*. According to another advantageous embodiment, the invention relates to the prevention or treatment of Salmonellosis caused by *S. typhimurium*.

According to a preferred embodiment, the RG-I polysaccharides containing composition is used to prevent or treat Salmonellosis in farm animals. According to a particularly preferred embodiment, said composition is used to prevent or treat Salmonellosis in poultry, e.g. chickens, ducks, goose or turkey. According to another particularly preferred embodiment, the composition is used to prevent or treat Salmonellosis in pigs.

According to another preferred embodiment, the RG-I polysaccharides containing composition is used to prevent or treat Salmonellosis in humans. Preferably, the RG-I polysaccharides containing composition is used to treat Salmonellosis in humans.

The RG-I polysaccharides that are employed in accordance with the present invention are preferably obtained from a plant source selected from apple, bell pepper, bilberry, carrot, citrus, grape, potato, sugar beet and olives and combinations thereof. More preferably, the RG-I polysaccharides are obtained from a plant source selected from apple (e.g. apple pomace), bell pepper, carrot (e.g. carrot pulp), citrus fruit (e.g. peel), grape, sugar beet (e.g.sugar beet pulp), olive (e.g. olive pulp), pea (e.g. pea pulp), potato (e.g. potato pulp) and combinations thereof. Even more preferably, the RG-I polysaccharides are obtained from a plant source selected from apple, carrot, olive and combinations thereof. Most preferably, the RG-I polysaccharides are obtained from apple and/or carrot.

The RG-I polysaccharides have a backbone that comprises rhamnogalacturonan-I stretches and optionally alpha (1,4)-linked homo-galacturonic acid stretches. The molar ratio of galacturonic acid residues to rhamnose residues in the RG-I polysaccharides is within the range of 20:1 to 1:1. Preferably the molar ratio of galacturonic acid residues to rhamnose residues in the RG-I polysaccharides ranges from 15:1 to 1:1, more preferably from 12:1 to 1:1, even more preferably from 10:1 to 1:1, most preferably from 9:1 to 1:1.

Preferably, rhamnose residues represent 3-50%, more preferably 5-50% and most preferably 10-50% of the monosaccharide residues in the backbone of the RG-I polysaccharides.

Rhamnose residues typically represent 3-50%, more preferably 3.5-40% and most preferably 4-35% of all the monosaccharide residues contained in the RG-I polysaccharides. i.e. including the monosaccharide residues that are contained in sidechains.

Galacturonic acid residues typically represent 50-97%, more preferably 50-95% and most preferably 50-90% of the monosaccharide residues in the backbone of the RG-I polysaccharides.

Galacturonic acid residues typically represent 10-80%, more preferably 15-70% and most preferably 20-65% of all the monosaccharide residues contained in the RG-I polysaccharides. i.e. including the monosaccharide residues that are contained in sidechains.

Arabinose residues typically represent 4-38%, more preferably 6-36% and most preferably 8-34% of all the monosaccharide residues contained in the carrot RG-I polysaccharides.

Galactose residues typically represent 4-42%, more preferably 8-40% and most preferably 10-38% of all the monosaccharide residues contained in the carrot RG-I polysaccharides.

The RG-I polysaccharides typically have a molecular weight of at least 10 kDa. Preferably, the RG-I polysaccharides have a molecular weight between 15 kDa and 2,000 kDa, more preferably between 20 kDa and 1,500 kDa, even more preferably between 35 kDa and 1,200 kDa, most preferably between 40 kDa and 1,000 kDa.

The average molecular weight of the RG-I polysaccharides that are contained in the present composition preferably exceeds 30 kDa, more preferably it exceeds 40 kDa and most preferably it exceeds 60 kDa.

Preferably, less than 85% of the galacturonic acid residues in the RG-I polysaccharides is esterified in the form of a methyl ester. More preferably, the RG-I polysaccharides have such a degree of esterification of between 0% and 70%, more preferably between 0% and 60%, even more preferably between 0% and 55%, most preferably between 0% and 50%.

Preferably, 0-95% of the galacturonic acid residues in the RG-I polysaccharides is esterified in the form of an acetyl ester. More preferably, the RG-I polysaccharides have such a degree of esterification of between 5% and 90%, more preferably between 7% and 50%, most preferably between 8% and 30%.

The backbone of the RG-I polysaccharides can comprise one or more side chains. These sidechains may contain residues of arabinose and/or galactose, and minor amounts of residues of the monomers fucose, glucose, glucuronic acid, xylose, and/or uronic acid. The one or more side chains preferably are selected from galactan side chains, arabinan side chains and arabinogalactan side chains.

The arabinan side chain comprises at least one or more alpha(1,5)-linked arabinose residues and is substituted at the O-4 position of a rhamnose residues in the RG-I domain. The arabinan side chain may be linear or branched. In case the side chain is linear, the side chain consists of alpha(1, 5)-linked arabinose residues. In case the arabinan side chain is a branched side chain, one or more alpha-arabinose residues are linked to the O-2 and/or O-3 of alpha(1,5)-linked arabinoses.

The galactan side chain comprises at least one or more beta(1,4)-linked galactose residues and is substituted at the O-4 position of a rhamnose residues in the RG-I domain.

The arabinogalactan side chain is substituted at the O-4 position of a rhamnose residue in the RG-I domain and can be a type I arabinogalactan (AGI) or a type II arabinogalactan (AGII). AGI is composed of a (1→4)-β-D-Galp backbone on which substitutions by monomeric Galp units at the O-6 or at the O-3 position can occur. AGI is further substituted with α-L-Araf-p residues and/or with (1→5)-α-L-Araf short side chains. AGII is composed of a(1→3)-β-D-Galp backbone decorated with (1→6)-β-D-Galp secondary chains, which are arabinosylated.

Preferably, arabinose residues and rhamnose residues are present in the RG-I polysaccharides in a molar ratio of less than 30:1, more preferably of less than 15:1, even more preferably of les than 8:1 and most preferably of less than :1.

Galactose residues and rhamnose residues are preferably present in the RG-I polysaccharides in a molar ratio of less than 30:1, more preferably of less than 15:1, even more preferably of less than 8:1 and most preferably of less than 5:1.

The combination of arabinose residues and galactose residues on the one hand and rhamnose residues on the other hand are typically present in the RG-I polysaccharides in a molar ratio of less than 40:1, more preferably of less than 20:1 and most preferably of less than 10:1.

The RG-I polysaccharides are preferably incorporated in the RG-I polysaccharides containing composition in the form of an pectic polysaccharide isolate that is enriched in RG-I polysaccharides. Accordingly, in a particularly preferred embodiment the RG-I polysaccharides represent at least 10 wt. %, more preferably at least 20 wt. %, even more preferably at least 30 wt. % and most preferably at least 40 wt. % of the pectic polysaccharides present in the RG-I polysaccharides containing composition.

Typically, the combination of galacturonic acid residues, rhamnose residues, arabinose residues and galactose residues constitutes at least 30 mol. % of the monosaccharide residues present in the saccharides that are contained in the RG-I polysaccharides containing composition. More preferably this combination constitutes at least 40 mol. %, even more preferably at least 45 mol. %, yet more preferably at least 50 mol. % and most preferably at least 70 mol. % of the monosaccharide residues in said saccharides.

In a particularly preferred RG-I polysaccharides containing composition, the combination of galacturonic acid residues and rhamnose residues represents at least 25 mol. %, more preferably 30-90 mol. %, most preferably 35-70 mol. % of the monosaccharide residues present in the saccharides that are contained in the RG-I polysaccharides containing composition.

Another aspect of the present invention relates to a method of preparing an edible composition, said method comprising mixing one or more edible ingredients with a polysaccharide component containing at least 5%, more preferably at least 10% and most preferably at least 15% by weight of dry matter of the RG-I polysaccharides as specified herein before.

According to a particularly preferred embodiment the RG-I polysaccharides represent at least 20 wt. %, more preferably at least 40 wt. %, even more preferably at least 50 wt. % and most preferably at least 60 wt. % of the pectic polysaccharides present in the polysaccharide component.

The polysaccharide component preferably is an isolate obtained from a plant source selected from apple, bell pepper, bilberry, carrot, citrus fruit, grape, sugar beet, olive, pea, potato and combinations thereof.

According to another preferred embodiment, the polysaccharide component has a water content of less than 6 wt. %, more preferably of less than 4 wt. % and most preferably of less than 2 wt. %.

The polysaccharide component preferably is a particulate material, e.g. a powder, a granulate or a pelletized material.

The polysaccharide component preferably contains less than 50%, more preferably less than 40% and most preferably less than 25% by weight of dry matter of sugars selected from glucose, fructose, sucrose and combinations thereof.

Yet another aspect of the invention relates to an edible composition that has been prepared by the present method.

Preferably, the edible composition contains 10-60 en. % protein and 5-50 en. % fat and 15-90 en. % carbohydrates.

According to another preferred embodiment, the edible composition contains:
1,000-2,500 IU/kg of vitamin A;
0.1-10 mcg/kg of vitamin B12;
100-350 IU/kg of vitamin D;
2-20 IU/kg of vitamin E; and
0.25-0.60 mg/kg of vitamin K.

The invention is further illustrated by the following non-limiting examples.

EXAMPLES

Example 1

A RG-I polysaccharide fraction was isolated from dry bell pepper powder (Paprika Mild 80-100 Atsa Steamtr- Felix Reverte S.A.) at pilot plant scale using the procedure described below.

The bell pepper material (100 kg) was washed three times under gentle steering with 80% aqueous ethanol, i.e. twice at 80° C. for 2 hours and then overnight at room temperature; each time using 12.5% (w/v), to remove ethanol soluble material. The ethanol insoluble residue was recovered every time by centrifugation (1000 G for 10 min). The ethanol insoluble residue obtained after the 3 wash cycles was dried and 90 kg was extracted twice with 1000 L hot water having a temperature of 95° C. for 90 minutes. Each time, the supernatant was retained after centrifugation at 1000 G for 10 minutes. The collected supernatant was subsequently filtered through cloth, and ultrafiltered using 2 KDa molecular weight cut off membranes to remove small molecular weight material. A dry RG-I enriched extract was obtained by drying the retentate, yielding approximately 5 kg of dry RG-I enriched polysaccharide extract.

Characterisation Of RG-I Polysaccharide Enriched Extract

The monosaccharide composition of the extract was determined after acid hydrolysis (methanolysis). Neutral monosaccharides were analysed using High Performance Anion Exchange Chromatography combined with Pulse Amperometric Detection (HPAEC-PAD). Uronic acids (Galacturonic acid being the dominant of uronic acids) were determined using the colorimetric m-hydroxydiphenyl assay.

The degree of acetylation and methylation was determined as follows:
Polysaccharide samples (2-5 mg) were treated with sodium hydroxide (0.1 M, overnight, 20° C.). Released methanol was measured by using head-space GC equipped with a DB-WAX ETR column, Cryo Focus-4 cold trap and FID detection (adapted from Huisman et al., Food Hydrocolloids, 18, 4, 2004, 665-668). The samples were neutralized (1 M HCl) and then the released acetyl was quantified by using HPLC equipped with an Aminex HPX 87H column with guard column and RI detection (adapted from Voragen et al.Food Hydrocolloids,1, 1, 1986, 65-70). Sugar beet pectin with known degree of methylation and acetylation was used as standard. Degree of esterification is expressed as molar amount of methanol and acetic acid released as percentage of the amount of uronic acid.

The molecular characteristics of the extract are shown in Table 1.

TABLE 1

|  | % mol/mol |
|---|---|
| Monosaccharides |  |
| Rha (Rhamnose) | 5.0 |
| GalA (Galacturonic acid) | 70.0 |
| Ara (Arabinose) | 9.0 |
| Gal (Galactose) | 9.0 |
| Glc (Glucose) | 2.0 |
| Xyl (Xylose) | 2.0 |
| Molecular Ratios |  |
| GalA/Rha | 7.78 |
| Ara/Rha | 1.71 |
| Gal/Rha | 1.59 |
| Degree of Methylation % | 32.0 |
| Degree of Acetylation % | 10.0 |

Example 2

Six week old specific pathogen free female C57BL/6 mice received ad libitum sterilized drinking water and a semi-synthetic irradiated AIN-93G diet (Research Diet Services, Wijk bij Duurstede, The Netherlands) with 30 mmol/kg calcium (uninfected and infected group) or the same food supplemented with 1% (w/w) of the RG-I enriched extract from bell pepper.

Mice were randomly assigned to treatment groups and housed with 3 mice per cage for 2 weeks and then individually for another week. The composition of the AIN-93G diet is described by Reeves et al. (*AIN-93 purified diets for laboratory rodents: final report of the American Institute of Nutrition ad hoc writing committee on the reformulation of the AIN-76A rodent diet.* J Nutr (1993)123: 1939-1951).

After 3 weeks dietary treatment mice were infected by gavage with 0.2 mL saline containing $10^8$ CFU of *S. enterica* serovar enteritidis (clinical isolate, phage type 4; strain NIZO1241, NIZO food research, Ede, the Netherlands). One group of mice was sham treated (uninfected, N=6) the other two groups were infected (infected; N=12 and test group infected; N=12).

Faeces was collected daily from the day of infection. Mice were euthanized and ileal samples were collected 4 days post infection. To quantify the number of viable *S. enterica* serovar enteritidis approximately 1 cm was cut from the middle of the ileum, opened longitudinally, and briefly flushed with saline. Faecal and ileal samples were homogenized in sterile saline and dilutions were plated for colony forming units (CFU) counts on Brilliant Green Modified plates (Becton Dickinson Diagnostics). Bacterial counts are expressed as the log CFU per gram wet weight. The results are summarized in Tables 2 and 3.

TABLE 2

| | $^{10}$log CFU of *Salmonella* recovered per gram of feces Day | | | | |
|---|---|---|---|---|---|
| | 0 | 1 | 2 | 3 | 4 |
| Control group - not infected | 0.00 ± 0.00 | 0.00 ± 0.00 | 0.00 ± 0.00 | 0.00 ± 0.00 | 0.00 ± 0.00 |
| Control group - infected | 0.0 ± 0.0 | 1.27 ± 0.39 | 0.92 ± 0.33 | 1.01 ± 0.37 | 1.76 ± 0.41 |
| Test group - infected | 0.0 ± 0.0 | 1.89 ± 0.34 | 0.16 ± 0.16 | 0.14 ± 0.14 | 0.00 ± 0.00 |

TABLE 3

| | $^{10}$log CFU of *Salmonella* recovered per gram of material from ilium, day 4 after infection. |
|---|---|
| Control group - not infected | 0.00 ± 0.00 |
| Control group - infected | 2.32 ± 0.44 |
| Test group - infected | 0.63 ± 0.46 |

Example 3

In a short-term simulation of the human colon the anti-pathogenic activity of RG-I polysaccharide from apple against *Salmonella enteritidis* was tested.

Apple RG-I polysaccharide was produced from dried apple pomace (residue of apple juice production, Greend-Fields, Poland), by aqueous extraction (10% w/w 2 hr 45° C.) using pectinase (Pectinex® Ultra Mash, Novozymes), heat inactivation (90° C., 10 min), removal of non-soluble residues by decanting, ultrafiltration (40 kDa cut of) and finally drying. Determination of monosaccharide composition was performed as described in Example 1. The results are shown in Table 4.

TABLE 4

| Rha (Rhamnose) | % mol/mol | 8 |
|---|---|---|
| GalA (Galacturonic acid) | % mol/mol | 18 |
| Ara (Arabinose) | % mol/mol | 48 |
| Gal (Galactose) | % mol/mol | 9 |
| Glc (Glucose) | % mol/mol | 10 |
| Xyl (Xylose) | % mol/mol | 6 |
| Total | | 99 |
| GlaA/Rha ratio | | 2.2 |
| Ara/Rha ratio | | 5.7 |
| Gal/Rha ratio | | 1.1 |
| % Methylation | | 27 |

A sugar-depleted base colon medium containing nutrients that are present in the colon (e.g. host-derived glycans such as mucin) was introduced into 70 mL penicillin bottles, already containing the test extracts (5 g/L final concentration). The bottles were sealed with rubber stoppers and anaerobiosis was achieved by flushing with $N_2$. Subsequently, a human fecal inoculum was prepared from a frozen fecal sample. After thawing, mixing with anaerobic phosphate buffer, homogenization, and removal of particles via centrifugation (2 min, 500 G), the fecal inoculum was added to the different bottles. The fecal inoculum was dosed at five-fold dilution as a technical simulation of a dysbiotic community. Additionally, a 2% inoculum of an overnight grown *Salmonella enteritidis* culture in BHI broth was added to the incubation (3.62 $10^7$ CFU/mL final concentration). At that point, the incubation started for a period of 48 h during which temperature was controlled at 37° C. and continuous mixing was ensured by a shaker (90 rpm). Samples were taken after 24 and 48 h incubation.

*Salmonella enteritidis* colonization was assessed using selective enumeration using selective McConckey agar dosed with 100 ppm streptomycin, for which the *Salmonella* strain is resistant. *Salmonella* species were differentiated from other bacteria due to their inability to utilize lactose resulting in non-pink colonies.

The sugar-depleted colon medium and inulin, a well-known prebiotic (Beneo, DP≥23, ~100% inulin), were used as negative and positive reference, respectively.

The results of the incubation experiments are shown in Table 5.

TABLE 5

| | Medium CFU/mL *$10^8$ | Inulin (reference) CFU/mL *$10^8$ | Apple RG-I CFU/mL *$10^8$ |
|---|---|---|---|
| 24 hr | 9.2 | 9.1 | 9.9 |
| 48 hr | 4.4 | 3.4 | 1.0 |

The invention claimed is:

1. A method of treating Salmonellosis in animals, comprising administering to an animal a composition, comprising:
   (i) at least 0.01%, by weight of dry matter, of rhamnogalacturonan I (RG-I) polysaccharides having a molecular weight of at least 20 kDa and a backbone consisting of galacturonic acid residues and rhamnose residues, the rhamnose residues being contained in alpha(1→4)-galacturonic-alpha(1→2)-rhamnose residues and
   (ii) pectic polysaccharides comprising at least 10% by weight of the RG-I polysaccharides, wherein:
   (a) rhamnose residues represent 4-35% of the monosaccharide residues contained in the RG-I polysaccharides;
   (b) galacturonic acid residues represent 20-70% of the monosaccharide residues contained in the RG-I polysaccharides;
   (c) the molar ratio of galacturonic acid residues to rhamnose residues in the RG-I polysaccharides is within the range of 9:1 to 1:1;
   (d) the molar ratio of arabinose residues to rhamnose residues in the RG-I polysaccharides is less than 8:1;
   (e) the molar ratio of galactose residues to rhamnose residues in the RG-I polysaccharides is less than 5:1;
   (f) the combination of arabinose residues and galactose residues and rhamnose are present in the RG-I polysaccharides in a molar ratio of less than 10:1;
   (g) 0-50% of the galacturonic acid residues in the RG-I polysaccharides is esterified in the form of a methyl ester;
   (h) 8-30% of the galacturonic acid residues in the RG-I polysaccharides is esterified in the form of an acetyl ester.

2. The method according to claim 1, wherein the pectic polysaccharides are branched polysaccharides.

3. The method according to claim 1, wherein the composition is administered at least once daily for at least 3 days in an amount providing at least 1 mg RG-I polysaccharides per kg of bodyweight of the animal per day.

4. The method according to claim 1, wherein the composition is administered to the animal prior to infection with *Salmonella*.

5. The method according to claim 1, wherein the Salmonellosis is caused by *Salmonella enterica* Serovar enteritidis.

6. The method according to claim 1, wherein the Salmonellosis is caused by Salmonella enterica Serovar typhimurium.

7. The method according to claim 1, wherein the animal is poultry.

8. The method according to claim 1, wherein the animal is a pig.

9. The method according to claim 1, wherein the animal is a human.

10. The method according to claim 1, wherein the composition further comprises:
- (iii) 1,000-2,500 IU/kg of vitamin A;
- (iv) 0.1-10 mcg/kg of vitamin B12;
- (v) 100-350 IU/kg of vitamin D;
- (vi) 2-20 IU/kg of vitamin E; and
- (vii) 0.25-0.60 mg/kg of vitamin K.

11. The method according to claim 1, wherein the combination of galacturonic acid residues, rhamnose residues, arabinose residues and galactose residues constitutes at least 30 mol % of the monosaccharide residues present in the saccharides that are in the composition.

12. The method according to claim 1, wherein the combination of galacturonic acid residues and rhamnose residues represents at least 25 mol % of the monosaccharide residues present in the saccharides that are in the composition.

13. The method according to claim 1, wherein the RG-I polysaccharides are obtained from apple, bell pepper, bilberry, carrot, citrus fruit, grape, potato, sugar beet, olive, pea or combinations thereof.

* * * * *